United States Patent
Lugnier et al.

(10) Patent No.: US 8,058,281 B2
(45) Date of Patent: Nov. 15, 2011

(54) USE OF ADENINE-DERIVED COMPOUNDS FOR THE TREATMENT OF LUPUS

(75) Inventors: Claire Renée Jeanne Lugnier, Strasbourg (FR); Sylviane Paule Ghislaine Muller, Strasbourg (FR); Fanny Sylvie Michèle Monneaux, La Wantzenau (FR); Jean-Jaques Bourguignon, Illkirch (FR)

(73) Assignee: Centre National de la Recherche Scientifique (CNRS) (FR)

( * ) Notice: Subject to any disclaimer, the term of this patent is extended or adjusted under 35 U.S.C. 154(b) by 0 days.

(21) Appl. No.: 12/224,733

(22) PCT Filed: Mar. 6, 2007

(86) PCT No.: PCT/EP2007/052084
§ 371 (c)(1),
(2), (4) Date: Feb. 24, 2009

(87) PCT Pub. No.: WO2007/101850
PCT Pub. Date: Sep. 13, 2007

(65) Prior Publication Data
US 2009/0221613 A1     Sep. 3, 2009

(30) Foreign Application Priority Data
Mar. 6, 2006 (FR) .................... 06 01958

(51) Int. Cl.
*A61K 31/52* (2006.01)

(52) U.S. Cl. ............. 514/263.4; 514/263.2; 514/263.22; 514/263.3

(58) Field of Classification Search .................. None
See application file for complete search history.

(56) References Cited

U.S. PATENT DOCUMENTS
6,716,987 B1    4/2004   Ohshima et al.
2003/0104974 A1  6/2003   Pitts et al.

FOREIGN PATENT DOCUMENTS
EP    1043021     10/2000
WO    2004014913   2/2004

OTHER PUBLICATIONS

Eisenberg, R., Journal Autoimmunity., 32(3-4), (May-Jun. 2009), pp. 223-230 (Abstract).*

Boichot Elisabeth et al:"Anti-inflammatory activities of a new series of selective phosphodiesterase 4 inhibitors derived from 9-benzyladenine" Journal of Pharmacology and Experimental Therapeutics, vol. 292, No. 2, (2000), pp. 641-653.
International Search Report, PCT/EP2007/052084.
Rahman et al., N. Engi. J Med., 358: 929-939, (2008).
Muller et al., Arthritis Rheum., 58(12): 3873-3883, (2008).
Sahebari et al., Arch. Iran Med.,13(2): 135-142, (2010).
Furrie et alt., Arthritis Res Ther., 10(5): R109, (2008).

* cited by examiner

*Primary Examiner* — Phyllis G. Spivack
(74) *Attorney, Agent, or Firm* — Lerner, David, Littenberg, Krumholz & Mentlik, LLP (57) ABSTRACT

The present invention is directed to a method of treating systemic lupus erythematosus comprising administering a compound of formula (I)

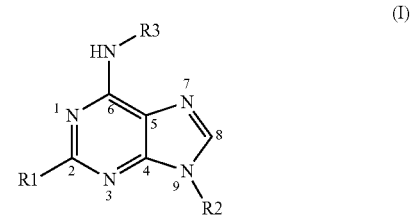

wherein
R1 is selected from the group consisting of $CF_3$, a $C_1$-$C_5$ alkyl, and $(CH_2)_n R4$, wherein n is between 0 and 4;
R2 is selected from the group consisting of $(CH_2)_m R4$ and $(CH_2)_m Ar$, wherein m is between 0 and 5;
R3 is selected from the group consisting of hydrogen and methyl;
R4 is selected from the group consisting of phenyl, OH, a $C_1$-$C_3$ alkoxy, a $C_1$-$C_3$ dialkylamino, piperidino, and N-methylpiperazino;
Ar represents

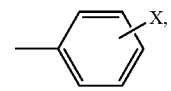

wherein X is selected from the group consisting of F, Cl, a $C_1$-$C_3$ alkoxy, and $CF_3$. The compounds can be used in combination with a second compound used in the treatment of systemic lupus erythematosus.

20 Claims, 4 Drawing Sheets

USE OF ADENINE-DERIVED COMPOUNDS FOR THE TREATMENT OF LUPUS

CROSS-REFERENCE TO RELATED APPLICATIONS

The present application is a national phase entry under 35 U.S.C. §371 of International Application No. PCT/EP2007/052084 filed Mar. 6, 2007, which claims priority from French Application No. 06 01958 filed Mar. 6, 2006, the disclosures of which are hereby incorporated herein by reference.

The invention relates to the use of adenine-derived compounds substituted in positions 2- and 9- and optionally N(6) of the adenine, for the manufacture of a drug for use in the treatment of systemic lupus erythematosus (SLE). The compounds can also be used in combination with a second compound used in the treatment of SLE.

Systemic lupus erythematosus (SLE) or disseminated lupus erythematosus is a highly polymorphous multigenic autoimmune disorder. It is the archetype non-organ-specific autoimmune disease. It affects on average 15-50 people per 100,000 in a year. In France, some 50,000 to 80,000 people are affected. It mainly affects women (about 9 out of 10 cases), and certain ethnic populations seem predisposed to developing the disease, notably Afro-Caribbean, Afro-American and Spanish-American populations.

Although the origin of the disease is not known, it is clear that it is a multifactor disease and different aetiological factors have been identified. As for genetic factors, susceptibility to the disease is clearly multigenic. Several genes have been shown to be implicated in genetic susceptibility, such as notably the DR2 and DR3 alleles of the HLA system. Other genes not related to the HLA system are also involved.

Moreover, environmental factors have been identified, such as ultraviolet radiation (photosensitive nature of lupus eruption) and sex hormones (women in periods of genital activity, role of and on pregnancy).

SLE is a highly polymorphic disease and its symptoms and clinical manifestations are thus very varied. Therefore, the disease is often difficult to diagnose. Diagnosis can only be made after detailed questioning and blood tests. In order to establish a diagnosis, the American Rheumatism Association (ARA) criteria are used. Four of these criteria must be present to confirm a diagnosis of lupus. These are present in 96% of SLE:

1. Facial rash in butterfly configuration
2. Discoid lupus eruption
3. Photosensitivity
4. Mouth or nasopharyngeal ulcers
5. Non-erosive polyarthritis
6. Pleuritis or pericarditis
7. Nephropathy: proteinuria >0.5 g/24 h or cylindruria
8. Seizures or psychosis
9. Hematological disorders: Haemolytic anaemia or leucopenia <4,000/mm$^3$ or lymphopenia <1,500/mm$^3$ or thrombocytopenia <100,000/mm$^3$
10. Immunologic abnormalities: presence of LE cells (Hargraves cells) or anti-native DNA antibodies (Abs) or anti-Sm antibodies or false positive syphilis result
11. Presence of a large number of antinuclear Abs Among clinical manifestations of lupus, lupus nephropathy disease is a frequent manifestation (estimated at between 35 and 55% using usual biological parameters) and is one of the main prognostic factors. It can be detected by testing for haematuria and/or leukocyturia with cylinders formation, high blood pressure, or most commonly, proteinuria. Detection of a nephrophaty disease is a turning point that influences the prognosis of the disease, because this can progress to chronic kidney failure within 5 to 10 years. In this case, patient survival can only be achieved with dialysis or a kidney transplant.

At the biological level, the characteristics of SLE are:
a generalised inflammatory syndrome during lupus flares, notably with a large amount of TNF-α secretion;
haematological disorders;
serological abnormalities, predominantly the existence of antinuclear antibodies (ANA) that can comprise anti-DNA, anti-histones, anti-nucleosomes, anti-Sm, anti-SSA or anti-SSB, and anti-ribonucleoprotein (RNP) antibodies. Patients also produce Abs directed against figured elements of the blood or phospholipids; some of these auto-Abs are able to participate in the formation of circulating immune complexes; and
hypocomplementemia linked to the use of complement by immune complexes (related to severe kidney failure that improves during remissions), and/or a constitutional deficit of C2 or C4 (predisposing to SLE).

Because the origin of the disease is as yet unknown, no specific treatment of SLE exists at the moment. Depending on the severity of the disease and on detected symptoms, a variety of alternative therapies are used.

For quiescent lupus, nothing more than simple monitoring is justified.

The treatment of minor forms affecting skin and joints is based on the use of non-steroid anti-inflammatory drugs (NSAIDs), for example aspirin (2 to 4 g daily), and synthetic antimalarials, for example hydroxychloroquine or chloroquine. NSAIDs reduce symptoms but present risks to the digestive system (stomach ulcers), risks of allergy, and risks to kidneys (kidney failure). The mode of action of synthetic antimalarials in lupus is poorly understood, but they are demonstrably effective. Hydroxychloroquine (Plaquenil®) is usually used at 400 mg/d. Effectiveness is judged after 3 months. However, annual eye testing (colour vision, Amsler scale) is needed to look for possible signs of toxicity to the retina, which is the main side effect of these compounds, and necessitates stopping treatment. Other side effects (e.g. neuromyopathy, agranulocytosis) are rarer.

Persistence of symptoms in joints can prompt the administration of a mild steroid treatment (less than 10 mg/d of prednisone). On the contrary, skin disorders that are resistant to antimalarials are not an indication for steroid treatment, but justify the use of other treatments (combination of antimalarials, thalidomide, . . . ).

Corticothery is used for visceral forms. Prednisone (Cortancyl® for example) is the standard corticosteroid. Broadly speaking, the dosage used is from 1 to 1.5 mg/kg/d in severe forms (diffuse proliferative glomerulonephritis, haemolytic anaemia) and 0.5 mg/kg/d in serositis. However, corticotherapy produces significant secondary effects, and some of these must be prevented. In particular, the role of corticotherapy in the acceleration of atherogenesis makes it necessary to take account of its various components (HBP, diabetes, dyslipidemia, smoking . . . ): a sodium-free, low glucidic diet is recommended, generally combined with potassium supplements. The preventive use of gastrointestinal protectants and curative treatment with anti-H2 reduces digestive complications, especially those arising from treatment in combination with NSAIDs. As for bones, osteoporosis seems to be reduced by adding vitamin D and calcium daily, alternating with diphosphonates. Risks of infection are considerably increased by high dose corticotherapy, which justifies detection and systematic treatment of latent foci of infection. In practice, initial phase corticotherapy is prescribed for 6 weeks to 3 months. The dose is progressively reduced by decreasing the previous dose by 10% every 5 to 15 days. Withdrawal, when this is attempted, must be preceded by investigation of the hypothalamic-hypophysial-suprarenal system. High doses of corticosteroids are administered as an intravenous bolus for treating severe flares, notably renal and neurological flares. Patients receive 500 mg-1 g of methylprednisolone (Solumedrol® for example) over 3 hours for 3 consecutive days, and this is then replaced by oral corticotherapy. It is thus clear that corticotherapy used in the most severe forms of SLE has a negative effect on the health and quality of life of patients.

In certain cases, immunosuppressive compounds are used. Immunosuppressive treatment in lupus disease requires careful judgement. This is because the risks (infections in the short-term, sterility, and possible oncogenesis in the long-term) mean that use of immunosuppressants is limited to severe visceral or corticosteroid-dependant forms. Various drugs are used in traditional protocols: cyclophosphamide (Endoxan® for example) at a dose of 2 to 3 mg/kg/day, azathioprine (Imurel® for example) at a dose of 2 to 4 mg/kg/day, for a duration of 6 months to 2 years. As well as the risks common to both drugs, cyclophosphamide has a greater tendency to cause cystitis and visceral cancers. Intermittent intravenous administration of cyclophosphamide (0.5 to 1 g/m$^2$ per month for 6 months then quarterly for 2 years) combined with medium dose corticotherapy is more effective than corticotherapy alone. This has been widely used in recent years.

It is clearly apparent from the above description that current treatments merely treat symptoms and lead to multiple side-effects that significantly affect the quality of life of patients. So no satisfactory treatment of SLE is available to date. Therefore new treatments need to be found that are capable of delaying the onset of the most severe manifestations, notably lupus nephropathy, decreasing their severity once they have appeared, and above all that do not cause such severe side-effects as current treatments.

Phosphodiesterases (PDE) form a superfamily comprising 11 families of enzymes responsible for the hydrolysis of cAMP and cGMP, second intracellular messengers, and thus play a major role in normal and pathological control of cellular response. Their fundamental role in intracellular signalling has made these enzymes new therapeutic targets. In the enthusiasm created by the discovery of these new targets and their varied distribution throughout tissues, a large amount of literature has been produced on potential therapeutic applications of PDE inhibitors. In particular, a great many patent applications have been filed concerning therapeutic applications of inhibitors of the different families of PDE. In almost all these patent applications, the therapeutic applications envisaged for inhibitors of a particular family of PDEs are extremely wide, covering many categories of disease, including vascular, neurological, haematological and inflammatory disorders, and a great many diseases are cited in each category. Notably, from the content of these patent applications, it would seem that SLE could be treated equally well by inhibitors of any one of the PDE families. Table 1 below refers to a certain number of patent applications that concern the possibility of using inhibitors of the various PDE families for treating lupus.

TABLE 1

Details of patent applications concerning the possibility of using inhibitors of the various PDE families for treating lupus

| PDE Family | Applicant | Publication No | Title |
|---|---|---|---|
| 1 | BAYER HEALTHCARE | WO04081563 | DIAGNOSTICS AND THERAPEUTICS FOR DISEASES ASSOCIATED WITH PHOSPHODIESTERASE 1A (PDE1A) |
| 2 | CELL PATHWAYS, INC. | WO03017926 | TREATMENT FOR LUPUS ERYTHEMATOSUS |
|  | BEAVO, JOSEPH, A. | WO0222661 | NOVEL PDES AND USES THEREOF |
| 3 | BAYER HEALTHCARE | WO04071377 | DIAGNOSTICS AND THERAPEUTICS FOR DISEASES ASSOCIATED WITH PHOSPHODIESTERASE 3A (PDE3A) |
| 4 | OHSHIMA ETSUO | U.S. Pat. No. 6,716,987 | DERIVATIVES OF BENZOFURAN OR BENZODIOXA2OLE COMPOUNDS |
|  | PITTS WILLIAM J ET AL. | US2003/04974 | DUAL INHIBITORS OF PDE7 AND PDE4 |
| 5 | WOOD, RALPH, E., | WO0202118 | METHOD OF TREATING PERIPHERAL VASCULAR DISEASES, PERIPHERAL NEUROPATHIES, AND AUTONOMIC NEUROPATHIES |
| 6 | AMBIT BIOSCIENCES CORPORATION | WO04110998 | PYRROLE COMPOUNDS AND USES THEREOF |
| 7 | DAIICHI SUNTORY PHARMA CO., LTD | WO04111053 | IMIDAZOTRIAZINONE DERIVATIVES AS PDE 7 (PHOSPHODIESTERASE 7) INHIBITORS |
| 8 | INCYTE GENOMICS, INC | U.S. Pat. No. 6,080,548 | CYCLIC NUCLEOTIDE PHOSPHODIESTERASES |
| 9 | INCYTE GENOMICS, INC | U.S. Pat. No. 5,922,595 | CYCLIC GMP PHOSPHODIESTERASE |
| 10 | INCYTE GENOMICS, INC | U.S. Pat. No. 6,416,991 | HUMAN CYCLIC NUCLEOTIDE PDES |
| 11 | BAYER HEALTHCARE | WO04029617 | DIAGNOSTICS AND THERAPEUTICS FOR DISEASES ASSOCIATED WITH PHOSPHODIESTERASE 11A (PDE11A) |

It is obviously not possible for the inhibitors of all PDE families to be really effective for treating such a specific and polymorphic disease as SLE. Moreover, with the exception of application WO03017926, which suggests using PDE2 inhibitors, and optionally PDE5 inhibitors, for the specific treatment of SLE, none of the applications mentioned in Table 1 above provide any result liable to encourage those skilled in the art to think that the inhibitors of the other families of PDE could really have any effect in the treatment of lupus.

Given the extremely prolific and discordant literature on PDE inhibitors and their potential therapeutic applications, it is clear that those skilled in the art would not be encouraged to look for an effective new compound for treating lupus among PDE inhibitors, with the possible exception of PDE2 inhibitors.

Moreover, more specifically concerning PDE4 inhibitors, it is important to emphasise that no document in prior art describes experimental results on SLE, but only results showing the ability of particular inhibitors described in these documents to inhibit allergic and inflammatory phenomena, or even in certain cases only their ability to inhibit the production of LPS-induced TNF-α.

Thus, U.S. Pat. No. 6,716,987 shows in the experimental part that claimed PDE4 inhibitor compounds have an inhibitory effect on several allergic and inflammatory phenomena that are completely different from SLE, and in particular on the production of LPS-induced TNF-α. No results concerning SLE are described.

In the same way, in patent application US2003/0104974, examples are given only for the ability of claimed compounds with a double inhibitory effect on PDE4 and PDE7 to inhibit LPS-induced TNF-α secretion.

Therefore, prior art documents concerning PDE4 inhibitors and claiming or generally suggesting their use in SLE treatment, only show in experiments an anti-inflammatory or anti-allergic action of the compounds claimed. No effect is described on components of lupus disease such as proteinuria or the presence of anti-DNA antibodies in serum, although these are fundamental components.

Those skilled in the art working in the domain of SLE treatment, aware of the complexity and of the polymorphic nature of lupus, would certainly not consider the results presented in the documents of prior art to be sufficient to encourage them to test PDE4 inhibitors in lupus treatment.

Patent application EP 1 043 021 describes adenine-derived compounds and their use as a selective inhibitor of the immune response of TH2 cells or as an anti-allergic agent.

Although therapeutic applications described in this patent application mainly concern TH2 response induced allergic disorders, lupus is also mentioned.

However, experimental examples only show that claimed compounds have an inhibitory effect on cytokine production by sensitised TH2 cells, on eosinophile infiltration, as well as an anti-allergic effect.

Therefore, no experimental result showing any effect of these compounds in a mechanism that is particularly important in SLE is described, and so the simple mention of lupus in the description would certainly not have encouraged those skilled in the art working in the domain of lupus treatment to test these compounds in SLE treatment.

However, surprisingly, the inventors were able to show the effectiveness in SLE treatment of adenine-derived compounds, substituted in positions 2- and 9-, and optionally N(6), of the adenine, and having the inhibitory abilities of enzymes of the PDE4 family. The inventors have indeed shown that these compounds are able to inhibit disease progression in MRL/lpr mice, the murine model of SLE, notably by countering nephropathy (decreasing of proteinuria), TNF-α production, and the production of anti-DNA auto-Abs, markers of the disease, thus leading to prolonged survival of MRL/lpr mice.

The inventors also compared the effect of these compounds to that of another adenine-derived PDE4 inhibitor, denbufylline, on the various components of lupus in MRL/lpr mice. The chemical formula of denbufylline is given below:

denbufylline

The obtained results obtained show that compounds according to the invention have a far greater effect than denbufylline for in vivo lupus treatment. Although denbufylline has a similar effect on the inhibition of TNF-α production, the effects of this compound on proteinuria or on the development of anti-DNA auto-antibodies, two of the fundamental components of lupus, are markedly lower than those of the compounds according to the invention or even inexistent.

Thus the inventors have shown a class of adenine-derived compounds, substituted in positions 2- and 9-, and optionally N(6), of the adenine, and show for the first time a real in vivo effect on all the components of this highly polymorphic disease, SLE.

Therefore the invention relates to the use of a compound of formula (I)

wherein
R1 is selected from $CF_3$, a $C_1$-$C_5$ alkyl, or $(CH_2)_n R4$ wherein n is between 0 and 4;
R2 is selected from $(CH_2)_m R4$ or $(CH_2)_m Ar$ wherein m is between 0 and 5;
R3 is selected from hydrogen or methyl;
R4 is selected from phenyl, OH, a $C_1$-$C_3$ alkoxy, a $C_1$-$C_3$ dialkylamino, piperidino, or N-methylpiperazino;
Ar represents wherein X is selected from F, Cl, a $C_1$-$C_3$ alkoxy, or $CF_3$;
or of a pharmaceutically acceptable salt, an enantiomer or a diastereoisomer thereof, or a mixture of these for the manufacture of a drug intended for the treatment of systemic lupus erythematosus.

The term "$C_1$-$C_i$ alkyl", $i \geq 1$, as used in the present application is intended to mean a linear or branched saturated hydrocarbon radical of the formula —$C_jH_{2j+1}$, where $1 \leq j \leq i$. Notably, a $C_1$-$C_5$ alkyl can be a $C_1$(methyl), $C_2$(ethyl), $C_3$(n-propyl, or isopropyl), C4(n-butyl, isobutyl, sec-butyl or tert-butyl), or $C_5$(e.g.: n-pentyl, neopentyl, isopentyl, tert-pentyl) alkyl. In the same way, a $C_1$-$C_3$ alkyl can be a $C_1$(methyl), $C_2$(ethyl) or $C_3$(n-propyl, or isopropyl) alkyl.

The term "$C_1$-$C_3$ alkoxy" as used herein is intended to mean a radical with the formula —O($C_1$-$C_3$ alkyl), where the $C_1$-$C_3$ alkyl is as defined above. Thus, the term includes methoxy, ethoxy, n-propyloxy and isopropyloxy radicals. Advantageous alkoxys in the invention are methoxy and n-propyloxy, in particular methoxy.

The term "$C_1$-$C_3$ dialkylamino" as used herein is understood to mean a radical with the formula —N($C_1$-$C_3$ alkyl)$_2$, where each $C_1$-$C_3$ alkyl independently is as described above. Advantageously, both $C_1$-$C_3$ alkyls are identical. Advantageous $C_1$-$C_3$ dialkylaminos in the invention have a formula selected from —N(CH$_3$)$_2$, —N(C$_2$H$_5$)$_2$, or —N(C$_3$H$_7$)$_2$.

Enantiomers and diastereoisomers are stereoisomers. The term "stereoisomers" as used herein is intended to mean isomers, that is to say compounds of the same empirical formula, having the same developed formula but a different spatial arrangement. "Enantiomers" are then stereoisomeric compounds that are mirror images of each other in a flat mirror, but not superimposable, while "diastereoisomers" are stereoisomers that are not enantiomers, that is to say that they are not stereoisomers that are mirror images of each other in a flat mirror. The scope of the invention extends to the different enantiomers and diastereoisomers of formula (I), and mixtures of these, notably a racemic mixture of stereoisomers.

The presence of a methyl group in position N(6) of the adenine improves the effectiveness of compounds defined above for the treatment of lupus. So in an advantageous embodiment, R3 is a methyl.

The presence of a benzyl substituent optionally substituted in position 9 of the adenine, improves the effectiveness of compounds previously defined for the treatment of lupus. So in an advantageous embodiment, R2 is (CH$_2$)Ar, wherein Ar is as previously defined. The X substituent of the Ar group can be in any position of the benzene ring. However, the X substituent of the Ar group is advantageously in position 2 of the benzene ring. Furthermore, X is advantageously selected from a fluorine atom and methoxy.

Particular compounds liable to be used for the manufacture of a drug directed to the treatment of SLE have been identified by the inventors. Notably, such advantageous compounds comprise compounds shown in Table 2 below.

TABLE 2

Advantageous compounds

| Compound name | Semi-developed formula* | Nomenclature name |
|---|---|---|
| NCS 613 |  | 9-(2-fluorobenzyl)-N(6)-methyl-2-trifluoromethyl-adenine |
| NCS 700 |  | 9-(2-methoxybenzyl)-N(6)-methyl-2-n-propyl-adenine |
| NCS 728 |  | 9-(2-methoxybenzyl)-N(6)-methyl-2-trifluoromethyl-adenine |
| NCS 658 |  | 9-(2-methoxybenzyl)-N(6)-methyl-2-methyl-adenine |

*Me = CH$_3$

A particularly advantageous compound is 9-(2-fluorobenzyl)-N(6)-methyl-2-trifluoromethyladenine (NCS 613).

Two synthesis routes can be used to prepare the compounds used according to the invention for the manufacture of a drug directed to the treatment of SLE.

The first is conventional, poorly convergent and uses chloropurine correctly substituted in position R$_2$, which is first alkylated with different alkyl halides (R$_2$X), then aminated by reaction with N-methylamine (see Diagram 1 below). More details about this method of preparation can be found in Bourguignon, J J et al., J. Med. Chem. (1997) 40, 1768-1770.

Diagram 1

The second synthesis route enables more systematic investigation of position 2 of the adenine by amination or coupling with palladium (0) (Suzuki, Sonogashira, Heck, Buchwald) starting from the corresponding 2-iodated derivative. The latter is obtained by treating the 2-amino derivative with isoamyl nitrite then with diiodo methane (see diagram 2 below). More details about this second synthesis route can be found in Raboisson P. et al., Eur. J. Med. Chem. (2003) 38, 199-214).

Diagram 2

The compounds described above can be used directly or as pharmaceutically acceptable salts. The term "pharmaceutically acceptable salt" as used herein is intended to mean notably salts from the addition of inorganic acids such as hydrochloride, sulphate, phosphate, diphosphate, bromhydrate and nitrate or organic acids such as acetate, maleate, fumarate, tartrate, succinate, citrate, lactate, methane sulphonate, p-toluenesulphonate, pamoate, oxalate and stearate. Also included in the scope of the present invention, when they are usable, are the salts formed from bases such as sodium or potassium hydroxide. For other examples of pharmaceutically acceptable salts, it is possible to refer to "Pharmaceutical salts", J. Pharm. ScL 66:1 (1977).

A drug directed to the treatment of SLE manufactured from a compound described above can further comprise a pharmaceutically acceptable carrier known to those skilled in the art. Such a drug can also contain any type of pharmaceutically acceptable excipient. These excipients can notably serve to improve the preservation of the compounds contained in the drug, their bioavailability, or to enable sustained release of active ingredients in the organism.

A drug directed to the treatment of SLE manufactured from a previously described compound can be administered by different routes, notably oral, nasal, rectal, intravenous, intramuscular, subcutaneous and topical routes. In particular, the characteristics of SLE include both systemic manifestations such as generalised inflammation, or circulation of immune complexes, and local manifestations, notably at skin and joints. The drugs according to the invention can therefore be used invasively or non-invasively, for example by intravenous, intramuscular, subcutaneous, oral, nasal or topical routes or by infiltration into joints.

The inventors have demonstrated that the compounds described above are particularly effective for the treatment of SLE. These compounds can thus be used alone. They can also be used in combination with a second compound that is useful for the treatment of SLE. Such compounds useful for the treatment of lupus are preferably selected from non-steroid anti-inflammatory drugs, synthetic antimalarials, corticosteroids or immunosuppressants. Thus, in one embodiment, the invention relates to the use of a compound such as previously defined, in combination with a second compound selected from non-steroid anti-inflammatory drugs, synthetic antimalarials, corticosteroids or immunosuppressants, for the manufacture of a drug directed to the treatment of systemic lupus erythematosus, to be administered simultaneously, separately, spread over a period of time or alternately.

Non-steroid anti-inflammatory drugs (NSAIDs) are fast acting symptom-treating drugs with analgesic, antipyretic and anti-inflammatory properties and which, despite their chemically heterogeneous natures, have a common mode of action: decrease in the production of prostaglandin (PG) and thromboxanes (TX) in the tissues, by inhibition of cyclooxygenase (COX), of which two isoenzymes exist (COX-1, which is constitutive and ubiquitous and COX-2, which can be induced in macrophage monocytes and polynuclear cells). The term NSAIDs as used herein is intended to mean NSAIDs themselves and salicylates, because they have almost all the same therapeutic effects and the same adverse effects. Useful NSAIDs in combination with a compound such as described above in a drug according to the invention comprise salicylate NSAIDs such as diflunisal, benorilate or aspirin; propionic derivatives such as alminoprofen, ketoprofen, ibuprofen, naproxen, flurbiprofen or tiaprofenic acid; indolic derivatives such as indomethacin, sulindac or etodolac; pyrazole derivatives such as phenylbutazone; oxicams such as piroxicam, tenoxicam, or meloxicam; selective anti-COX2 agents such as rofecoxib or celecoxib; or other NSAIDs such as diclofenac, nimesulide, niflumic acid, mefenamic acid, or nabumeton. Preferably, the NSAID used in combination with a compound described above is selected from aspirin, indomethacin and ibuprofen.

Synthetic antimalarials that can be combined with a 9-benzyladenine-derived compound described above in a drug according to the invention comprise 4-methanolquinolines such as quinine and mefloquine; 4-aminoquinolines such as chloroquine, hydroxychloroquine and amodiaquine; 8-aminoquinolines such as primaquine; biguanides such as proguanil; sulphonamides combined with diaminopyrimidines such as sulphadoxine/pyrimethamine; sesquiterpene lactones such as artemisinin and derivatives. Preferably, the synthetic antimalarial used in combination with a compound described above is selected from chloroquine and hydroxychloroquine, preferably hydroxychloroquine.

Corticosteroids include natural corticosteroids (cortisone and hydrocortisone) and their synthetic derivatives. Corticosteroids useful in combination with a 9-benzyladenine derivative described above in a drug according to the invention comprise cortisone, hydrocortisone, prednisone, prednisolone, methylprednisolone, fluorinated triamcinolone, dexamethasone, betamethasone, paramethasone, triamcinolone, cortivazol, and tetracosactide. Prednisone remains the gold standard corticosteroid in lupus treatment and is used preferentially. When a corticosteroid is used in combination with a compound as described above in a drug according to the invention, a salt-free, diabetic type diet (low sugar and low calorie) and potassium, calcium and vitamin D supplements are vital.

Immunosuppressants that can be combined with a 9-benzyladenine-derived compound described above in a drug according to the invention comprise cyclosporine, tacrolimus, azathioprine and cyclophosphamide. Preferably, the immunosuppressant used in combination with a previously described compound is selected from azathioprine and cyclophosphamide.

When a drug directed to the treatment of SLE is prepared from a compound as described above and from a second compound useful in the treatment of SLE, these active compounds can be administered simultaneously, separately, spread over a period of time or alternately. This means that the drug resulting from the combination of the compounds can be presented in the form of a single drug, so that each time it is taken the two compounds are necessarily administered "simultaneously", or else in the form of two distinct drugs each comprising one of the compounds, in which case the drugs can be administered "separately" (at the same time, but in two separate units, optionally by two separate routes), or "spread over a period of time" (where both units are administered at different times, several hours or several days apart). These different possibilities make it possible to take account of the particular properties of the different compounds. Furthermore, the two compounds can be administered "alternately", that is to say that the patient is treated first by a cure of one of the compounds, then by a cure of the second compound, and so on, alternately.

DESCRIPTION OF THE DRAWINGS

FIG. 4: Effect of compound NCS 613 and denbufylline on anti-double-stranded DNA Abs. The presence of Abs directed against DNA in murine serums was measured at different ages (in weeks) by ELISA. Results are shown as a percentage of positive mice. A mouse is defined as positive when the optical density (OD) measured by ELISA is greater than 1.

EXAMPLES

Example 1

Biological Effects of Compound NCS 613 and Comparison with the effects of another PDE4 inhibitor, Denbufylline 1.1 Materials and Methods 1.1.1 Animal Experiments: In Vivo Study of the Effect of the Administration of Compound NCS 613 or Denbufylline Administration and Samples Pre-autoimmune female MRL/lpr mice aged 5 weeks received by intravenous route, either buffered saline (PBS; control group, 100 μl per mouse), or compound NCS 613, (30 μg/100 μl per mouse, diluted in saline solution containing 10% ethanol), or denbufylline (100 μg/100 μl per mouse, diluted in saline solution containing 10% ethanol). The two groups were composed of 10 mice each. The administrations (4 in number) were carried out at the ages of 5, 7, 9 and 13 weeks, and mice were monitored regularly (observations, proteinuria test by Albutix strip, blood tests).

Measurement of Anti-DNA Antibodies in Serum.

The presence of Abs directed against DNA in murine serums was measured at different ages by ELISA (Monneaux et al., Eur. J. Immunol. (2003) 33, 287-296; Monneaux et al, Arthritis Rheum (2004) 50, 3232-3238.). Calf thymus double-stranded DNA (Sigma) was adsorbed (100 ng/ml) on 96 well polyvinyl chloride plates (Falcon) and incubated overnight at 37° C. After three washes and a saturation step in PBS-Tween buffer containing bovine serum albumin, serums (diluted to 1/500) were incubated for one hour at 37° C. The bonds between the Abs present in the serum and DNA were revealed by incubation with a secondary Ab (peroxidase coupled anti-mouse IgG), followed by incubation with peroxidase substrate and a chromogen. The absorbance was measured at 450 nm by spectrophotometry after the reaction had been stopped.

Measurement of TNF-α Secretion by Blood Cells from Treated Mice after LPS Stimulation.

TNF-α secretion was measured after bacterial lipopolysaccharide (LPS) stimulation of mouse blood cells (blood pooled from the 7 mice per group). LPS cell stimulation for 24 hours generates TNF-α secretion which can then be measured in culture supernatants. Cells from the blood of the 3 groups of mice were separated on a Ficoll gradient, and then stimulated by LPS. Supernatants were collected after 24 hours of culture, and the presence of TNF-α in supernatants was measured by a double sandwich ELISA test (BD Biosciences). This experiment was carried out at different ages (11 and 14 weeks, that is 2 weeks after the 3$^{rd}$ administration and 1 week after the 4$^{th}$ administration respectively).

1.1.2 Patient Study: Ex Vivo Study of the Effect of Compound NCS 613 on the Production of TNF-α

The blood of 5 patients with lupus, rheumatoid arthritis or Sjögren's syndrome was collected directly in heparinated tubes. Mononuclear blood cells were separated by centrifugation (30 min at 600 g) on a Ficoll gradient. Cells were then grown at a concentration of $2\times10^5$ cells per well in the presence or absence of compound NCS 613 (10 µM) for 45 minutes then stimulated with LPS. Supernatants were recovered after 24 hours of culture and the level of TNF-α in supernatants was measured by double sandwich ELISA (BD Biosciences).

1.1.3 Study of Cyclic Nucleotides Phosphodiesterases Phosphodiesterase Activity

Cyclic nucleotides phosphodiesterase activity was measured by a radioenzyme method using tritiated cyclic AMP or GMP (1 µM) as substrate (Lugnier C. et al., Biochem. Pharmacol. (1986) 35, 1743-1751; Keravis T et al., Meth. Mol. Biol. (2005) 307, 63-74.). Tritiated adenosine or guanosine monophosphate formed by hydrolysis of the labelled cyclic nucleotide was transformed, in a second incubation with excess nucleotidase, into tritiated adenosine or guanosine. The formed nucleoside was separated from nucleotides by anion exchange resin chromatography. The radioactivity of the nucleoside was measured by liquid scintillation. Enzyme incubations were carried out under conditions in which there was no more than 15% of substrate hydrolysis, and each point was repeated.

Isolation of PDE1, PDE3, PDE4 and PDE5

A 3 g piece of bovine aortic media was chopped up with scissors, homogenised using an Ultra-Turrex then using a glass/glass Potter in 7 volumes/weight of buffer A containing a cocktail of protease inhibitors (20 mM Tris-HCl, 0.25 M saccharose, 2 mM magnesium acetate, 1 mM dithiothreitol, 5 mM EGTA, 2000 U/ml aprotinine, 10 mg/l leupeptine and 10 mg/l soy-bean trypsin inhibitor). The homogenate was centrifuged at 105.000 g for an hour. The supernatant was passed through a DEAE-Sephacel column (15×1.6 cm) which had been equilibrated with buffer B (buffer A without saccharose, EGTA and protease inhibitors). The column was washed until no absorption at 280 nm could be detected, then elution was with a linear NaCl gradient (0-0.5 M) in buffer B. 3 ml fractions were collected and enzymatic activity was measured under various conditions so as to determine the peaks of enzymatic activity contained in the fractions for, in the order of elution, PDE1, PDE5, PDE3 and PDE4. Each fraction was aliquoted and stored at −80° C.

Isolation of PDE2

Washed human platelets from the French Blood Bank (Etablissement Francais du Sang) in Strasburg were left to stand, then the sedimented cells were homogenised in buffer A and centrifuged at 105.000 g for 1 hour. The supernatant was subject to chromatography following the procedure already described for the aortic media (C-2). Then the fractions rich in PDE2 (activity stimulated by 5 µM cGMP) were subject to HPLC chromatography using Pharmacia's MonoQ H/R 5×5. The fraction containing PDE2 was aliquoted and stored at −80° C. (Kameni Tcheudji J. F et al, J. Mol. Biol. (2001) 310, 181-791.).

Activity and Pharmacological Profile of Molecules

Determination of $IC_{50}$

The concentration of the substance causing 50% inhibition of enzymatic activity ($IC_{50}$) at 1 µM substrate was calculated by non-linear regression (Prism, GraphPad) with the help of the results obtained for compound concentrations that varied as the molecule concentration was increased from 1 nM to 300 µM. Because of solubility problems, the maximum concentration used in this study was limited to 300 µM.

Determination of $IC_{50}$ for the whole group from PDE1 to PDE5 allowed characterisation of the specificity of the molecule for its target.

1.2 Results 1.2.1 PDE4c-Selective Inhibitory Capacity of Compound NCS 613

The selectivity of compound NCS 613 and denbufylline for different families of PDE enzymes was analysed. The results given in Table 3 below show that the compound is selective for the PDE4 family of enzymes.

TABLE 3

Effects of compound NCS 613 on PDEs isolated from vascular tissue ($IC_{50}$, µM)

| Analysis | PDE1 | PDE2 | PDE6 | PDE4 | PDE5 |
|---|---|---|---|---|---|
| NCS 613 | 39 | 24 | n.s. | 0.042 | 4.7 |
| Denbufylline | 33 | 208 | n.s | 0.76 | 5.4 | n.s.: $IC_{50} > 300$ µM.

Moreover, the selectivity of compound NCS 613 for the 4 types of PDE4 enzymes (A, B, C, D) was also tested. The results given in Table 4 below show that this compound is selective for the PDE4C subtype.

TABLE 4

Effects of compound NCS 613 on the recombinant subtypes of PDE4 ($IC_{50}$, nM)

| Compound | PDE4A | PDE4B | PDE4C | PDE4D |
|---|---|---|---|---|
| NCS 613 | 43 | 50 | 1.4 | 14 |

1.2.2 Effect of the Administration of Compound NCS 613 or Denbufylline to Pre-Autoimmune Mice on the Development of the Disease The in vivo study of biological properties of NCS 613 compound was carried out in pre-autoimmune MRL/lpr mice. In these mice, the presence of a mutation known as lpr which concerns the Fas gene (membrane receptor involved in cells entering apoptosis) leads to an autoimmune condition, which, although it is similar to human lupus in terms of clinical and biological signs developed, is more severe than the condition observed in humans. A feature of the MRL/lpr mouse line is a lympho-proliferative syndrome associated with vascular lesions, arthritis and glomerulonephritis leading to death of the mouse. The disease appears early in MRL/lpr mice (50% mortality at 20 weeks) and the first clinical signs (proteinuria) appear from the age of 13-14 weeks. As in human lupus, auto-Abs directed against nuclear complexes (spliceosome and nucleosome) are present in these MRL/lpr mice. Therefore, the MRL/lpr mouse line is a very good murine model for systemic lupus erythematosus. However, another feature of MRL/lpr mice is the development of arthritis accompanied by rheumatoid factors similar to another human autoimmune disease, rheumatoid arthritis. Around the age of 3-4 months, 45% of MRL/lpr mice have infiltrations into the synovium with joint erosion.

The in vivo effects of the compound NCS 613 on the various components of lupus in MRL/lpr mice were further compared to the effects of another adenine-derived PDE4 inhibitor, denbufylline.

Effects on Proteinuria

Figure 1:
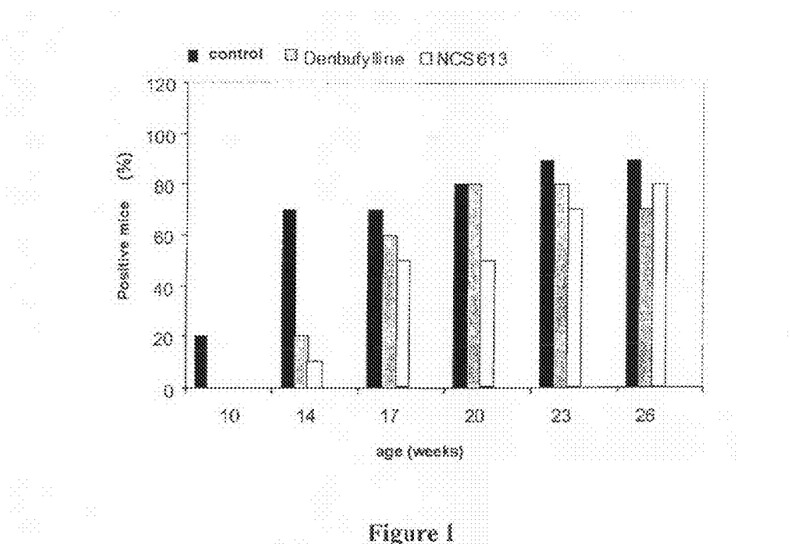
FIG. 1: Effect of compound NCS 613 and denbufylline on proteinuria in MRL/lpr mice. Up to the age of 13 weeks, the mice received 4 administrations either of 30 μg of compound NCS 613 or of 100 μg of denbufylline. The results show the percentage of mice with positive proteinuria as a function of the age (in weeks) of the mice used.

Observation of clinical parameters shows that the administration of compound NCS 613 up to the 13$^{th}$ week delays the appearance of proteinuria. At 14 weeks, proteinuria is detected in only 10% of mice treated with compound NCS 613, compared to 70% of control mice. Moreover, after the end of the treatment, proteinuria is still lower in mice treated with compound NCS 613. At 20 weeks, proteinuria is detected in only 50% of mice treated with compound NCS 613, compared to 80% of untreated control mice (see FIG. 1).

Thus, during the phase of treatment with compound NCS 613 (up to 13 weeks), treated mice are protected from the onset of proteinuria, whereas proteinuria is detected in certain untreated control mice from as early as 10 weeks. After the end of the treatment with compound NCS 613, the number of mice in which proteinuria is detected remains smaller until 26 weeks, which is 13 weeks after the end of treatment.

Therefore, when chronically administered, compound NCS 613 seems to prevent the onset of proteinuria in MRL/lpr mice.

On the contrary, results obtained with denbufylline, another adenine-derived PDE4 inhibitor with a different chemical structure, show that denbufylline does not significantly delay the onset of proteinuria, since, contrary to mice treated with compound NCS 613, at 20 weeks mice treated with denbufylline have proteinuria equivalent to that of control mice.

Thus, contrary to denbufylline, another PDE4 inhibitor, compound NCS 613 significantly decreases proteinuria of MRL/lpr mice, and the development of proteinuria is a key factor in the progression of SLE, this highly polymorphic disease.

Effect on Life Expectancy

The obtained results show that the administration of NCS 613 has a beneficial effect on the survival of MRL/lpr mice.

Figure 2:
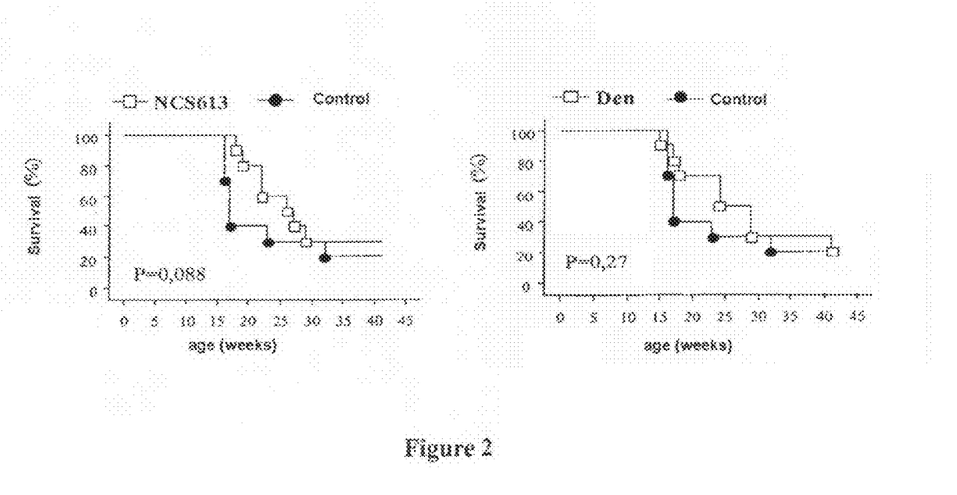
FIG. 2: Effect of compound NCS 613 (A) and denbufylline (B) on survival of MRL/lpr lupus mice. Up to the age of 13 weeks, the mice received 4 administrations either of 30 μg of compound NCS 613 or of 100 μg of denbufylline. The results are expressed in percentage survival of mice. Control mice received only PBS (phosphate buffered saline, pH 7.4) without the active ingredient.

Indeed, compound NCS 613 markedly prolongs the life expectancy of mice at 20 weeks (p=0.0581), and this effect continues to a lesser degree at 26 weeks (p=0.0881; see FIG. 2A). It greatly increases the half-life of auto-immune mice since mortality at 21 weeks is only 30% as compared to 60% mortality in the untreated control group (see FIG. 2A).

On the contrary, denbufylline has no acknowledged effect on mouse survival, since mortality begins at 15 weeks and is almost identical to that of the control mice at 26 weeks (p=0.27, see FIG. 2B).

Effect on TNF-α Secretion

Ex vivo inhibition of TNF-α secretion was measured after bacterial lipopolysaccharide (LPS) stimulation of mouse blood cells (blood pooled from the 7 mice per group). This experiment was carried out on mice of different ages (11 and 14 weeks, that is 2 weeks after the 3$^{rd}$ administration and 1 week after the 4$^{th}$ administration respectively).

Figure 3:
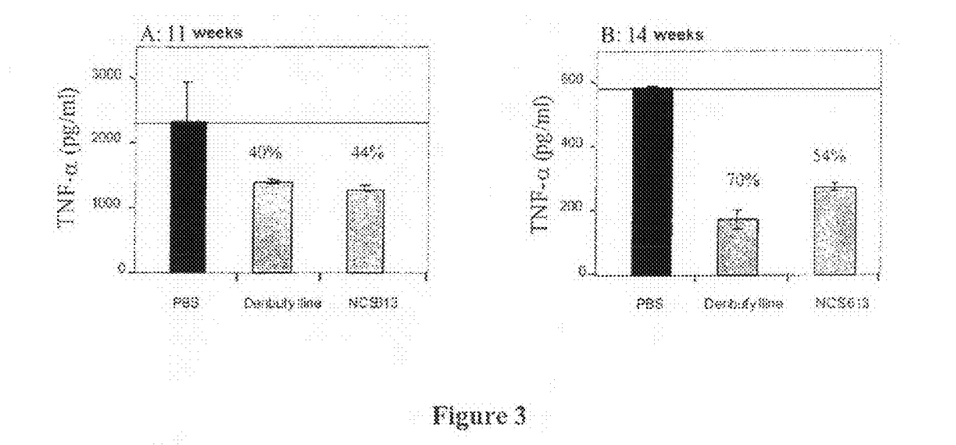
FIG. 3: Effect of compound NCS 613 and denbufylline on the production of TNF-α by blood cells from treated mice after LPS stimulation. TNF-α secretion by blood cells from mice having received saline solution (PBS), compound NCS 613 or denbufylline after ex vivo LPS stimulation for 24 hours was measured in the supernatants by ELISA. The error bars show the standard deviation of duplicates, and the percentage inhibition of TNF-α secretion as a function of the secretion measured in the PBS group is shown. The figures refer to experiments carried out on mice aged 11 (A) and 14 (B) weeks.

Results show that mouse blood cells that had recently received compound NCS 613 produced less TNF-α in response to LPS than blood cells from untreated control group mice (see FIG. 3). The inhibition percentage of TNF-α secretion in blood cells of mice treated with compound NCS 613 as compared to blood cells of the PBS control group was 44% at 11 weeks, and 54% at 14 weeks (see FIG. 3).

Equivalent results were obtained with denbufylline (see FIG. 3). At 14 weeks, the inhibition obtained with denbufylline was even greater than that obtained with compound NCS 613.

Figure 4:
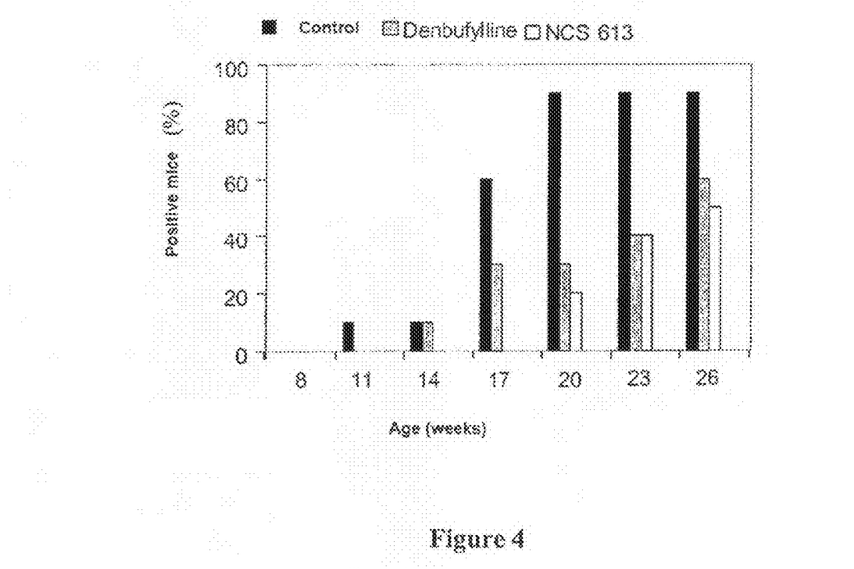

Effect on the Production of Anti-Double-Stranded DNA Antibodies, Markers for Lupus Results (see FIG. 4) show that the presence of anti-DNA Abs in serum was apparent from the age of 11 weeks and was detectable in practically all untreated lupus mice (controls) at the age of 20 weeks. Compound NCS 613 delays the appearance of these Abs at the age of 20 weeks, and furthermore, they appear in a smaller number of mice (20%). At 26 weeks, i.e. 13 weeks after the end of treatment, only 50% of mice treated with compound NCS 613 were positive for the presence of anti-DNA Abs in serum, as compared to 90% in control group.

Although denbufylline reduced the percentage of positive mice, its effects were much less marked than those of compound NCS 613. The first positive mice appeared from 14 weeks (only 1 week after stopping treatment) as compared to 20 weeks for the compound NCS 613. Furthermore, at 26 weeks, the percentage of positive mice remained smaller in the group treated with compound NCS 613.

The presence of anti-DNA Abs in serum is an important manifestation of the highly polymorphic disease that is SLE. In this aspect, the obtained results clearly indicate the superiority of compound NCS 613 compared to denbufylline, another adenine-derived PDE4 inhibitor.

Conclusion

All these results show that the administration of compound NCS 613 to pre-autoimmune MRL/lpr mice decreases the capacity of blood cells to secrete TNF-α in response to mitogenic stimulation of bacterial origin and slows the progression of disease in treated mice by decreasing proteinuria and production of anti-DNA Ab.

Thus, compound NCS 613 effectively acts on all the components of the highly polymorphic disease that is SLE.

On the contrary, denbufylline (100 µg), another adenine-derived PDE4 inhibitor, has an effect equivalent to that of the compound NCS 613 (30 µg) only on the inhibition of TNF-α secretion in response to LPS stimulation, but has much weaker or even inexistent effects on the other components of the disease such as proteinuria and anti-DNA antibody production, which leads to a much smaller effect on the survival of MRL/lpr mice.

Globally, these results therefore show that the inventors have revealed a class of compounds that are particularly useful for in vivo treatment of SLE since it combats all the components of this disease.

1.2.3 Effect of Compound NCS 613 on TNF-α Secretion after LPS Stimulation of Mononuclear Blood Cells of Autoimmune Patients.

Mononuclear blood cells from patients with systemic autoimmune diseases including lupus (SLE), rheumatoid arthritis (RA) and Sjögren's syndrome (Goug) were incubated in the presence or absence of NCS 613, then stimulated with LPS, and TNF-α secretion was measured.

Figure 5:
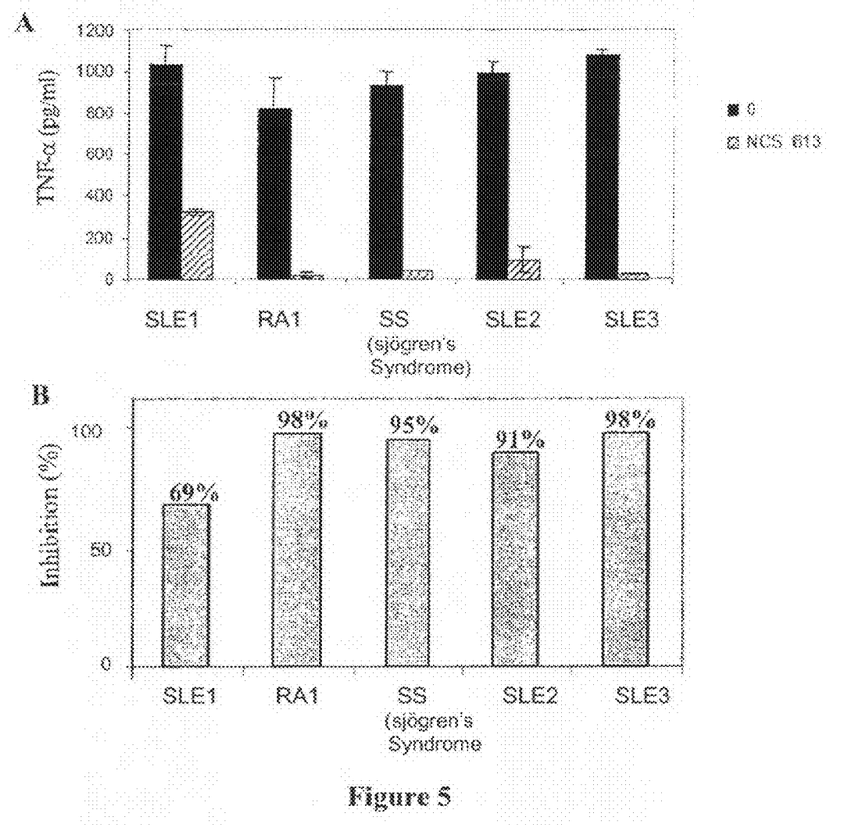
FIG. 5. Inhibition of TNF-α secretion by compound NCS 613 after LPS stimulation of the PBMCs of patients with auto-immune diseases. Blood cells from patients with lupus (SLE), rheumatoid arthritis (RA) and Sjögren's syndrome (SS) were incubated for 45 minutes in the presence or absence of NCS 613 (10 μM), then stimulated with LPS. The supernatants were recovered after 24 hours of culture and the level of TNF-α in supernatants was measured by ELISA. The results are given in TNF-α concentration after incubation in the presence or absence of NCS 613 (A) or as inhibition of TNF-α secretion after incubation with NCS 613 (B). Error bars show the standard deviation of duplicates.

Results (see FIG. 5 clearly) show that compound NCS 613 used at a concentration of 10 µM very significantly inhibits (approximately 70 to 98%) the production of TNF-α by blood cells of autoimmune patients, stimulated by bacterial lipopolysaccharides (LPS). In particular, the inhibition percentage of TNF-α secretion by mononuclear blood cells of lupus (SLE) patients is 69%, 91%, and 98% (a mean of 86%).

This result obtained in humans agrees with those obtained in a murine model of lupus and shows that compound NCS 613 is able to inhibit the ability of LPS stimulated mononuclear blood cells from lupus patients to secrete inflammatory cytokine TNF-α, which is characteristic of the inflammatory syndrome caused by SLE.

1.2.4 Effect of Compound NCS 613 on Basal TNF-α Secretion by Mononuclear Blood Cells of a Lupus Patient Of the 3 lupus patients studied, one had a basal TNF-α secretion, in the absence of LPS stimulation. So the ability of compound NCS 613 to inhibit basal TNF-α secretion was studied in blood cells of this patient.

Figure 6:
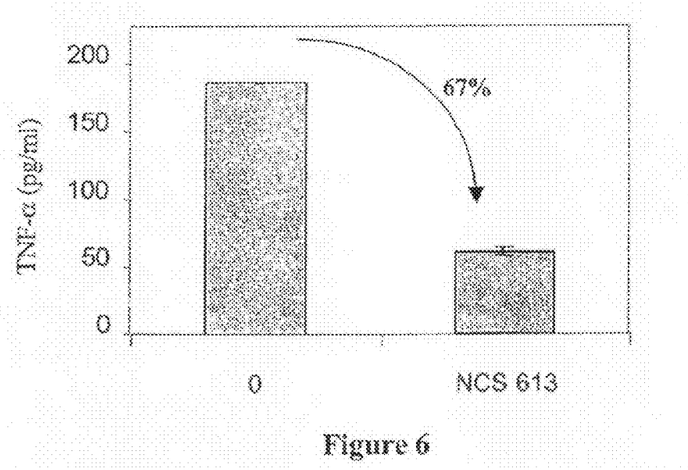
FIG. 6: Inhibition of TNF-α secretion by PBMCs of a lupus patient after incubation with NCS 613. The blood cells of a lupus patient (LED2) were incubated in the presence or absence of NCS 613 (10 μM). Supernatants were recovered after 24 hours of culture and the level of TNF-α in the supernatants was measured by ELISA. The results are given as TNF-α concentration after incubation in the presence or absence of NCS 613 and the percentage inhibition of TNF-α secretion after incubation with NCS 613 is shown. Error bars show the standard deviation of duplicates.
Figure 7:
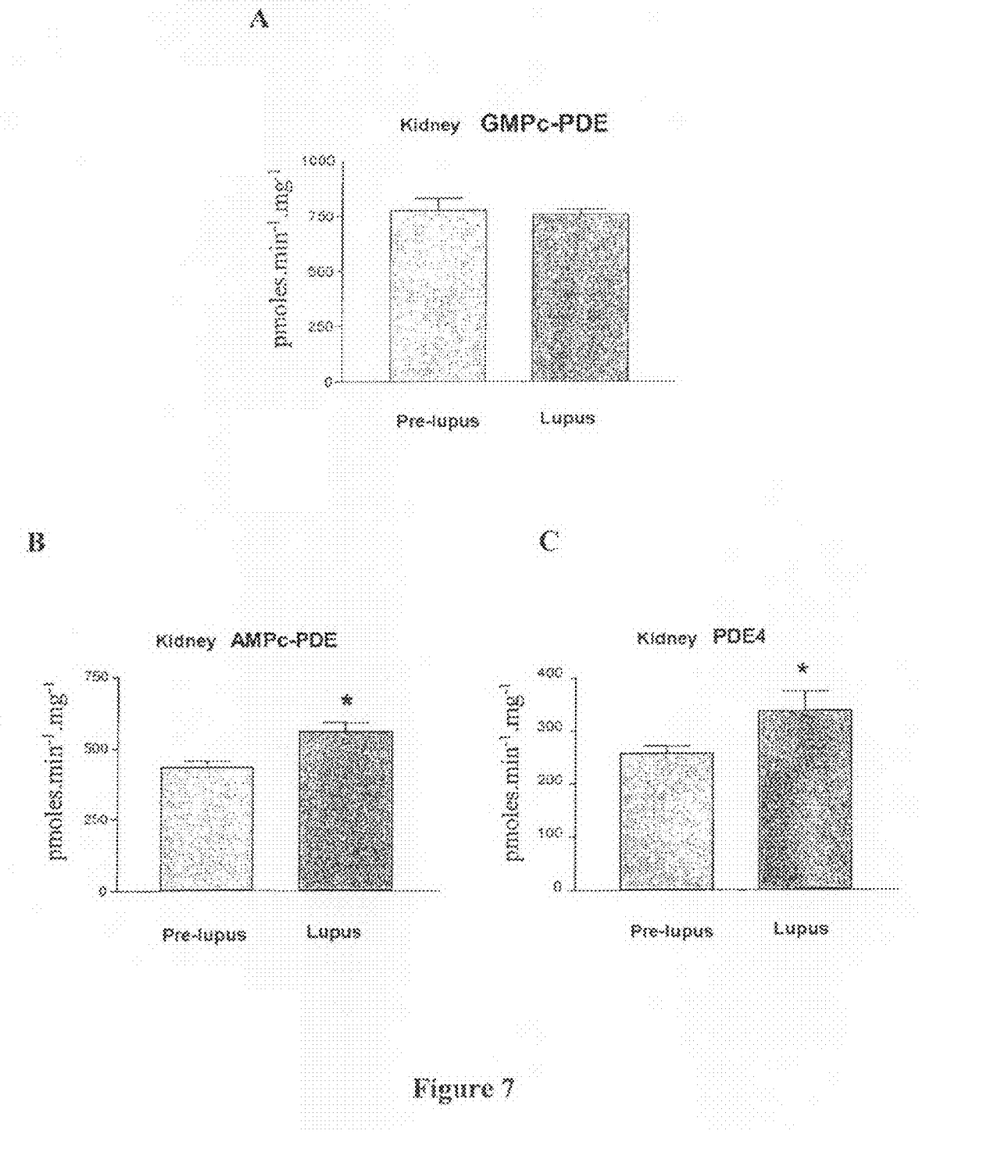
FIG. 7. Variation of phosphodiesterase activity in renal tissue as lupus sets in. Hydrolytic activity of cGMP (A), cAMP (B), as well as PDE4 activity (C) were compared in pre-lupus mice (8 weeks, n=3) and lupus mice (18 weeks, n=3). The results are means of results obtained on the three mice ±s.e.m. expressed in pmol·min$^{-1}$·mg$^{-1}$*$P<0.05$ compared to pre-lupus tissue.

Results presented in FIG. 6 show that compound NCS 613 inhibited 67% of the spontaneous TNF-α secretion by blood cells from a lupus patient.

Therefore, compound NCS 613 is effectively able to inhibit TNF-α secretion by mononuclear blood cells of a patient with SLE.

1.3 Conclusions

All results obtained in lupus mice show with no ambiguity that compound NCS 613 prevents the development of lupus, by delaying and decreasing proteinuria and marker anti-DNA Abs production, decreasing the inflammatory response and increasing the survival of treated mice. Its beneficial effect continues long after stopping treatment, suggesting that long-term treatment could be even more effective.

These results are specific to compound NCS 613 and its derivatives. The use of another adenine-derived PDE4 inhibitor, denbufylline, did not produce comparable results. Although denbufylline is able to inhibit TNF-α secretion caused by LPS, it does not have an effect comparable to that of compound NCS 613 on proteinuria inhibition and on the production of anti-DNA antibodies. Thus, the inventors have revealed a class of compounds that are particularly effective for in vivo treatment of SLE.

Furthermore, the effect of NCS 613 on the inflammatory response of lupus patients and patients with systemic autoimmune diseases such as rheumatoid arthritis and Sjögren's syndrome suggests that compound NCS 613 is potentially able to treat lupus and other autoimmune diseases.

Example 2

Correlation Between PDE4 Activity in Kidney and the Development of Lupus in MRL/Lpr Mice.

2.1 Material and Methods

After sacrifice of pre-lupus (8 weeks, n=3) and lupus mice (18 weeks, n=3), kidneys were removed and frozen in liquid nitrogen, then kept at −80° C. until enzyme activity determination. Kidneys were then ground individually in liquid nitrogen, using a cryogrinder, then homogenised in a pH 7.5 buffer containing a cocktail of protease inhibitors. The protein content was determined by Lowry method and the hydrolytic activity of PDEs using a radioenzyme method, individually for each mouse organ.

The assay measures the transformation of tritiated cAMP or cGMP respectively into tritiated adenosine or guanosine, after addition of an excess of 5'nucleotidase. Formed tritiated nucleosides were separated from cyclic nucleotides by ion exchange chromatography and quantified by liquid scintillation.

The contribution of PDE4 to the total hydrolytic activity of cAMP was determined by carrying out the assay in the presence or absence of 10 µM of rolipram, a specific PDE4 inhibitor (Keravis and coll., 2005).

2.2. Results

As lupus sets in, there is an increase in the hydrolytic activity of cAMP without any change in the hydrolytic activity of cGMP, suggesting that only enzymes that specifically hydrolyse cAMP are modified by lupus. Moreover, this increase is specifically associated with an increase in PDE4 activity, which contributes by more than 50% to cAMP hydrolysis activity.

Therefore, the results show for the first time a genuine correlation between an increase in PDE4 activity in kidney and the development of lupus disease. Those skilled in the art could not have anticipated this exact result.

REFERENCES

Bourguignon, J. J et al., J. Med. Chem. (1997) 40, 1768-1770.
Raboisson P. et al., Eur. J. Med. Chem. (2003) 38, 199-214).
"Pharmaceutical salts", J. Pharm. Sci. 66:1 (1977).
Monneaux F. et al., Eur. J. Immunol. (2003) 33, 287-296.
Monneaux, F. et al., Arthritis Rheum (2004) 50, 3232-3238.
Lugnier C. et al., Biochem. Pharmacol. (1986) 35, 1743-1751.
Keravis T et al., Meth. Mol. Biol. (2005) 307, 63-74.
Kameni Tcheudji J. F et al., J. Mol. Biol. (2001) 310, 181-791.

The invention claimed is:

1. A method for treating systemic lupus erythematosus in a subject in need thereof, comprising administering to said subject an efficient amount of a compound of formula (I)

wherein

R1 is selected from the group consisting of $CF_3$, a $C_1$-$C_5$ alkyl, and $(CH_2)_n R4$ wherein n is between 0 and 4;

R2 is selected from the group consisting of $(CH_2)_m R4$ and $(CH_2)_m Ar$ wherein m is between 0 and 5;

R3 is selected from the group consisting of hydrogen and methyl;

R4 is selected from the group consisting of phenyl, OH, a $C_1$-$C_3$ alkoxy, a $C_1$-$C_3$ dialkylamino, piperidino, and N-methylpiperazino;

Ar represents wherein X is selected from the group consisting of F, Cl, a $C_1$-$C_3$ alkoxy, and $CF_3$;

or of a pharmaceutically acceptable salt, an enantiomer or a diastereoisomer thereof, or a mixture of these.

2. The method according to claim 1, wherein R3 is methyl.

3. The method according to claim 1, wherein R2 is $(CH_2)$Ar.

4. The method according to claim 3, wherein substituent X of the Ar group is in position 2.

5. The method according to claim 4, wherein said substituent X is selected from the group consisting of F and $OCH_3$.

6. The method according to claim 1, wherein R3 is methyl and R2 is $(CH_2)$Ar.

7. The method according to claim 6, wherein substituent X of the Ar group is in position 2.

8. The method according to claim 7, wherein said substituent X is selected from the group consisting of F and $OCH_3$.

9. The method according to claim 1, wherein the compound is selected from the group consisting of 9-(2-fluorobenzyl)-N(6)-methyl-2-trifluoromethyladenine, 9-(2-methoxybenzyl)-N(6)-methyl-2-n-propyladenine, 9-(2-methoxybenzyl)-N(6)-methyl-2-trifluoromethyladenine, and 9-(2-methoxybenzyl)-N(6)-methyl-2-methyladenine.

10. The method according to claim 9, wherein the compound is 9-(2-fluorobenzyl)-N(6)-methyl-2-trifluoromethyladenine.

11. A method for treating systemic lupus erythematosus in a subject in need thereof, comprising administering to said subject an efficient amount of a first compound according to Formula (I), and a second compound selected from the group consisting of non-steroid anti-inflammatory drugs, synthetic antimalarials, corticosteroids and immunosuppressants, wherein said first and second compounds are administered simultaneously, separately, spread over a period of time, or alternately, wherein R1 is selected from the group consisting of $CF_3$, a $C_1$-$C_5$ alkyl, and $(CH_2)_n R_4$ wherein n is between 0 and 4;
R2 is selected from the group consisting of $(CH_2)_m R_4$ and $(CH_2)_m Ar$ wherein m is between 0 and 5;
R3 is selected from the group consisting of hydrogen and methyl;
R4 is selected from the group consisting of phenyl, OH, a $C_1$-$C_3$ alkoxy, a $C_1$-$C_3$ dialkylamino, piperidino, and N-methylpiperazino;
Ar represents wherein X is selected from the group consisting of F, Cl, a $C_1$-$C_3$ alkoxy, and $CF_3$;
or of a pharmaceutically acceptable salt, an enantiomer or a diastereoisomer thereof, or a mixture of these.

12. The method according to claim 11, wherein the second compound useful for the treatment of lupus is selected from the group consisting of aspirin, ibuprofen, indomethacin, hydroxychloroquine, prednisone, cyclophosphamide, and azathioprine.

13. The method according to claim 11, wherein in the first compound, R3 is methyl.

14. The method according to claim 11, wherein in said first compound, R2 is $(CH_2)Ar$.

15. The method according to claim 14, wherein substituent X of the Ar group is in position 2.

16. The method according to claim 15, wherein said substituent X is selected from the group consisting of F and $OCH_3$.

17. The method according to claim 11, wherein in said first compound, R3 is methyl and R2 is $(CH_2)Ar$.

18. The method according to claim 17, wherein substituent X of the Ar group is in position 2.

19. The method according to claim 18, wherein said substituent X is selected from the group consisting of F and $OCH_3$.

20. The method according to claim 11, wherein the first compound is selected from the group consisting of 9-(2-fluorobenzyl)-N(6)-methyl-2trifluoromethyladenine, 9-(2-methoxybenzyl)-N(6)-methyl-2-n-propyladenine, 9-(2-methoxybenzyl)-N(6)-methyl-2trifluoromethyladenine, and 9-(2-methoxybenzyl methoxybenzyl)-N (6)-methyl-2-methyladenine.

* * * * *